US012738368B2

(12) United States Patent
Moon et al.

(10) Patent No.: US 12,738,368 B2
(45) Date of Patent: Sep. 15, 2026

(54) METHOD OF AND APPARATUS FOR PROVIDING INFORMATION ON MEDICAL PERSONNEL

(71) Applicant: SAMSUNG LIFE PUBLIC WELFARE FOUNDATION, Seoul (KR)

(72) Inventors: Jung Hwan Moon, Seoul (KR); Ihn Seon Lee, Seoul (KR); Jun Young Choi, Seoul (KR); Ji Hye Woo, Seoul (KR); Chae Yeon Park, Seoul (KR); Ho Jun Seol, Seoul (KR); Do Hoon Lim, Seoul (KR); Sei Yeul Oh, Seoul (KR); Hyun Jung Ko, Seoul (KR); Mi Ja Ju, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 215 days.

(21) Appl. No.: 18/396,950

(22) Filed: Dec. 27, 2023

(65) Prior Publication Data

US 2024/0371502 A1 Nov. 7, 2024

(30) Foreign Application Priority Data

May 2, 2023 (KR) ........................ 10-2023-0056954

(51) Int. Cl.
*G16H 20/40* (2018.01)
*G16H 40/20* (2018.01)

(52) U.S. Cl.
CPC .................................. *G16H 40/20* (2018.01)

(58) Field of Classification Search
CPC .. G16H 40/20; G06Q 10/06; G06Q 10/06398; G06Q 10/10; G06Q 10/063112;
(Continued)

(56) References Cited

U.S. PATENT DOCUMENTS

2020/0350065 A1 11/2020 Inukai et al.
2021/0307864 A1 10/2021 Wolf et al.
(Continued)

FOREIGN PATENT DOCUMENTS

WO 2021/181212 A1 9/2021

OTHER PUBLICATIONS

Extended European Search Report issued in EP Application No. 23220705, dated Jun. 20, 2024.

*Primary Examiner* — Maroun P Kanaan
(74) *Attorney, Agent, or Firm* — DILWORTH IP, LLC

(57) ABSTRACT

A method of providing information on medical personnel may be provided. The method according to an embodiment may include: receiving surgical information including information on a medical treatment department performing a surgery, information on an operating surgeon, surgical category information, and surgical code information; determining a score for each item that constitutes the surgical information on medical personnel on the basis of information on on-duty records of the medical personnel; determining a medical personnel score corresponding to the surgical information on the basis of a weighted value corresponding to the score for the each item; and providing information on the medical personnel that includes the medical personnel score.

18 Claims, 11 Drawing Sheets

(58) Field of Classification Search
CPC .. G06Q 10/06393; G06Q 10/105; H04W 4/02
See application file for complete search history.

(56) References Cited

U.S. PATENT DOCUMENTS

| | | | | |
|---|---|---|---|---|
| 2021/0313052 | A1* | 10/2021 | Makrinich | G11B 27/28 |
| 2022/0375583 | A1 | 11/2022 | Hosny et al. | |
| 2023/0114135 | A1* | 4/2023 | Wiggermann | G16H 40/20<br>705/7.42 |
| 2023/0402167 | A1* | 12/2023 | Tiwary | G16H 20/40 |

* cited by examiner

FIG. 1A

PHASE OF COMPUTERIZING ON-DUTY RECORDS OF SURGICAL NURSES

PHASE OF AUTOMATICALLY ASSIGNING NURSE

FIG. 2A

| NURSE | WORK STARTING TIME | WORK ENDING TIME | OPERATING ROOM | MEDICAL TREATMENT DEPARTMENT | OPERATING SURGEON | SURGICAL CODE | SURGERY TIME |
|---|---|---|---|---|---|---|---|
| KANG OO | 2023-02-21 07:00 | 2023-02-21 15:30 | E03 | DIVISION OF PULMONARY AND CRITICAL CARE MEDICINE | KIM OO | IM3000005 | 00:31 |
| | | | | | | IM3D00006 | 00:50 |
| | | | | | | IM3D00012 | 00:56 |
| | | | | DIVISION OF THORACIC SURGERY | SIM OO | TSSC00093 | 01:52 |
| JEON OO | 2023-02-21 07:00 | 2023-02-21 15:30 | E05 | DIVISION OF HEPATO-BILIARY-PANCREATIC SURGERY | HEO OO | GSSC00016 | 01:06 |
| | | | | | | | 01:58 |
| | | | | DIVISION OF BREAST SURGERY | YU OO | GSSD00432 | 03:30 |
| KIM OO | 2023-02-22 07:00 | 2023-02-22 15:30 | E06 | DEPARTMENT OF UROLOGY | JEONG OO | UROD00237 | 01:31 |
| | | | | | | UROC00160 | 04:09 |
| HONG OO | 2023-02-22 15:00 | 2023-02-22 23:30 | B11 | DEPARTMENT OF NEUROSURGERY | JEONG OO | NSS000007 | 05:36 |
| CHOE OO | 2023-02-22 15:00 | 2023-02-22 23:30 | C16 | DIVISION OF CARDIOVASCULAR SURGERY | KIM OO | TSS000010 | 06:51 |
| MIN OO | 2023-02-22 23:00 | 2023-02-23 07:30 | D20 | DEPARTMENT OF SURGERY | CHOE OO | GSSC00007 | 01:51 |
| | | | | | | GSSC00006 | 02:17 |
| | | | | | | GSSC00454 | 02:05 |
| ⋮ | | | | | | | |

FIG. 2B

| NURSE | MEDICAL TREATMENT DEPARTMENT | SURGICAL CODE | TIME REQUIRED FOR SURGERY |
|---|---|---|---|
| LEE OO | DEPARTMENT OF NEUROSURGERY | NSS000007 | 6.1 |
| | DEPARTMENT OF PLASTIC AND RECONSTRUCTIVE SURGERY | PSS000505 | 10 |
| | DIVISION OF THORACIC SURGERY | TSS000093 | 2.9 |
| ⋮ | | | |

| | MEDICAL TREATMENT DEPARTMENT (WEIGHTED VALUE a%) | OPERATING SURGEON (WEIGHTED VALUE b%) | SURGICAL CATEGORY (WEIGHTED VALUE c%) | SURGICAL CODE (WEIGHTED VALUE d%) | SCORE |
|---|---|---|---|---|---|
| NUMBER OF TIMES OF PARTICIPATION (WEIGHTED VALUE $\alpha$%) | $X_1 = x_1 * a\% * \alpha\%$ | $X_2 = x_2 * b\% * \alpha\%$ | $X_3 = x_3 * c\% * \alpha\%$ | $X_4 = x_4 * d\% * \alpha\%$ | $X = X_1 + X_2 + X_3 + X_4$ |
| PARTICIPATION TIME (WEIGHTED VALUE $\beta$%) | $Y_1 = y_1 * a\% * \beta\%$ | $Y_2 = y_2 * b\% * \beta\%$ | $Y_3 = y_3 * c\% * \beta\%$ | $Y_4 = y_4 * d\% * \beta\%$ | $Y = Y_1 + Y_2 + Y_3 + Y_4$ |
| TOTAL | | | | | $X+Y$ |

FIG. 3A

| SURGICAL CODE | NURSE | NUMBER OF TIMES OF PARTICIPATION | PARTICIPATION TIME | DEPARTMENT OF SURGERY | NURSE | NUMBER OF TIMES OF PARTICIPATION | PARTICIPATION TIME |
|---|---|---|---|---|---|---|---|
| GSSD00478 | YUN OO | 121 | 456.9 | DIVISION OF HEPATO-BILIARY-PANCREATIC SURGERY | LEE OO | 253 | 1243.5 |
| | JEONG OO | 91 | 371.2 | | U OO | 211 | 1051.2 |
| | CHOE OO | 50 | 256.3 | | JEONG OO | 198 | 1092.3 |
| | KIM OO | 38 | 192.5 | | CHOE OO | 167 | 989.9 |
| | MUN OO | 19 | 89.7 | | JANG OO | 154 | 768.6 |
| | PARK OO | 7 | 42.4 | | KO OO | 132 | 612.8 |
| | ⋮ | ⋮ | ⋮ | | ⋮ | ⋮ | ⋮ |

Figure 4:
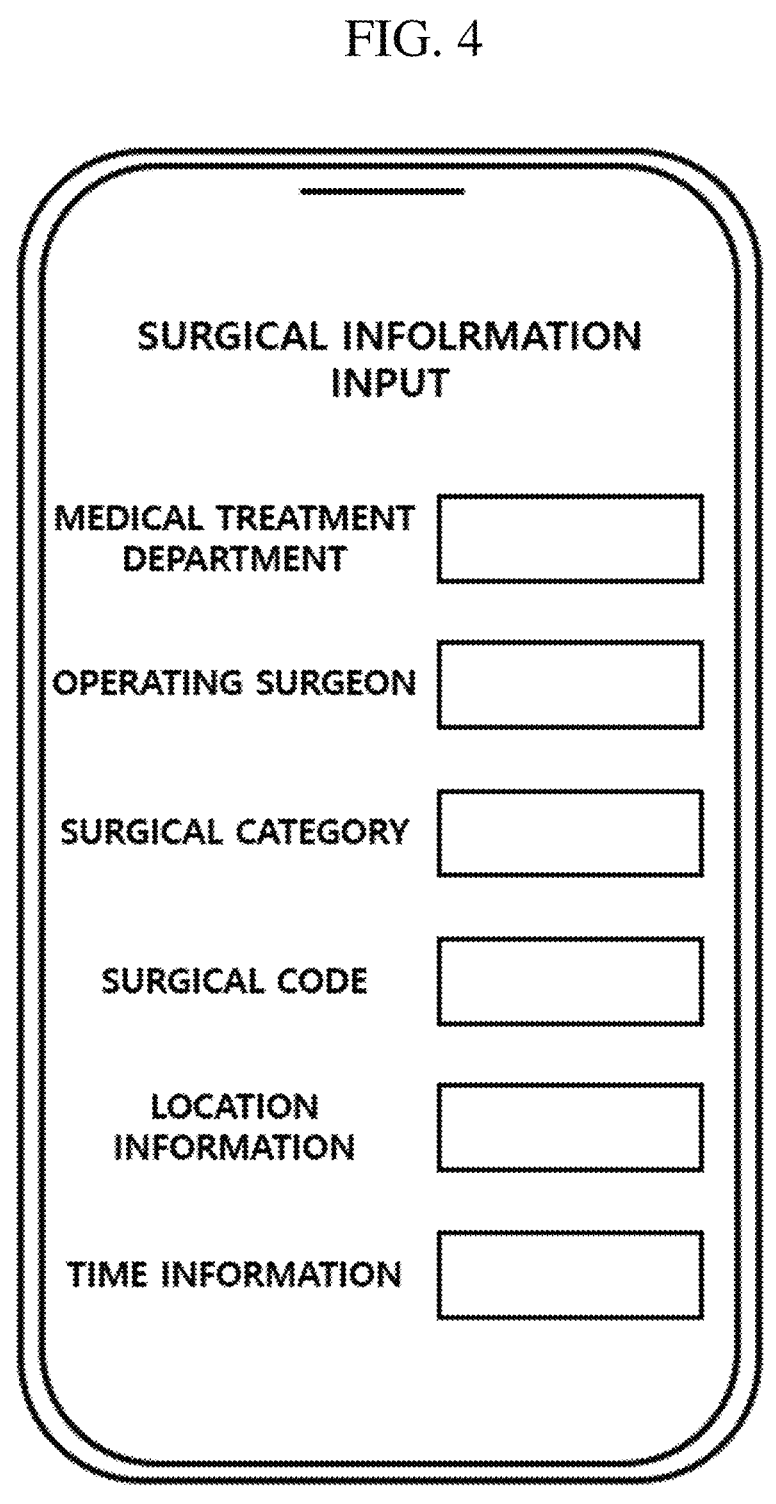

SURGICAL INFOLRMATION INPUT

MEDICAL TREATMENT DEPARTMENT

OPERATING SURGEON

SURGICAL CATEGORY

SURGICAL CODE

LOCATION INFORMATION

TIME INFORMATION

Figure 6:
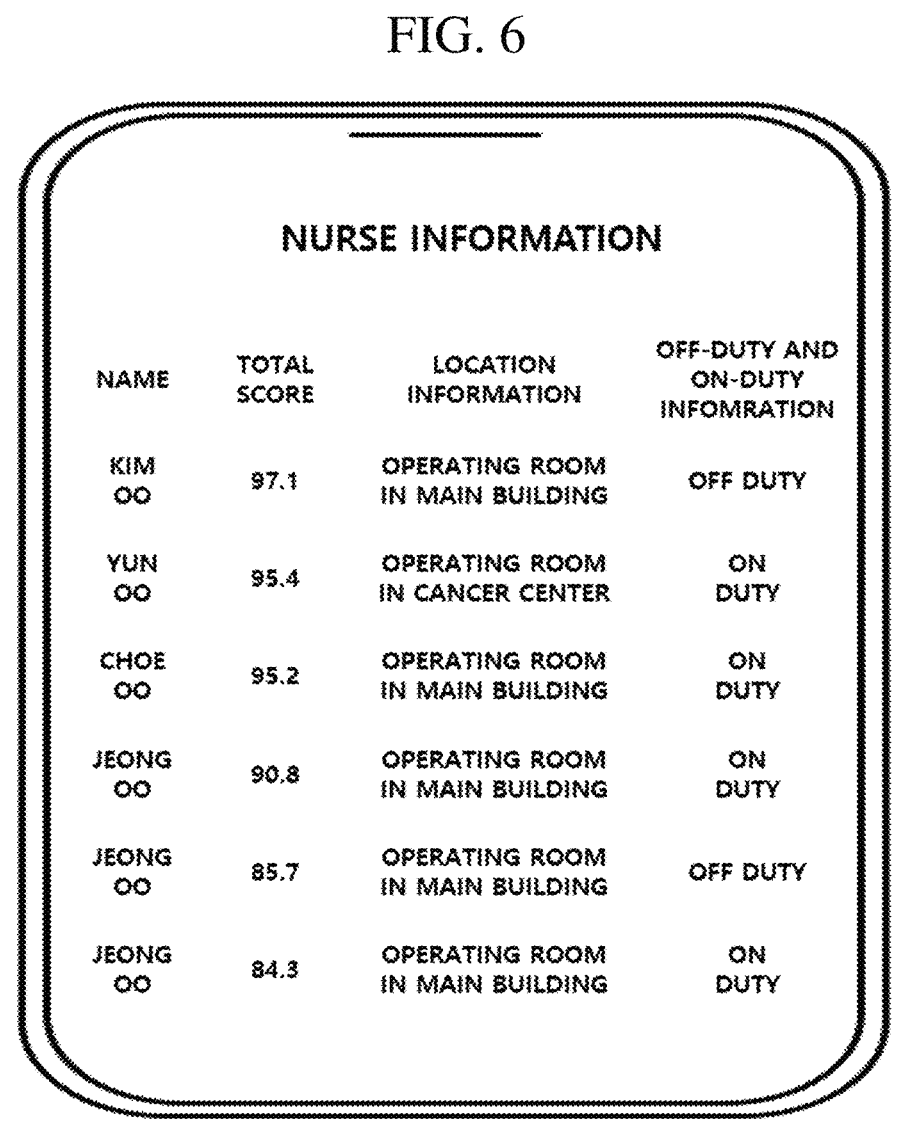

NURSE INFORMATION

| NAME | TOTAL SCORE | LOCATION INFORMATION | OFF-DUTY AND ON-DUTY INFOMRATION |
|---|---|---|---|
| KIM OO | 97.1 | OPERATING ROOM IN MAIN BUILDING | OFF DUTY |
| YUN OO | 95.4 | OPERATING ROOM IN CANCER CENTER | ON DUTY |
| CHOE OO | 95.2 | OPERATING ROOM IN MAIN BUILDING | ON DUTY |
| JEONG OO | 90.8 | OPERATING ROOM IN MAIN BUILDING | ON DUTY |
| JEONG OO | 85.7 | OPERATING ROOM IN MAIN BUILDING | OFF DUTY |
| JEONG OO | 84.3 | OPERATING ROOM IN MAIN BUILDING | ON DUTY |

METHOD OF AND APPARATUS FOR PROVIDING INFORMATION ON MEDICAL PERSONNEL

BACKGROUND

1. Technical Field

The present disclosure relates to a method of providing information on medical personnel, and more particularly, to a method of providing information for assigning medical personnel suited for performing surgeries.

2. Related Art

Operating rooms are independent special departments within hospital organizations. Medical treatments are conducted with systematic teamwork under strict control in a limited environment in the operating rooms. In recent years, along with the trend of fragmentation and specialization in the surgical field, advancement of cutting-edge surgical instruments and equipment has led to operating room nurses, as capable professionals with complex special skills in addition to surgical techniques, taking on expanded roles.

Accordingly, when performing a specific surgery, assignment of a surgical nurse best suited for the surgery in question is an important factor for ensuring a smooth surgical process and a process of performing a medical treatment on a surgical patient. However, in a case where the operating room in which the surgical nurse works and the history of the surgery in which the surgical nurse participates are manually managed, missing information may occur. In a case where the surgical nurse is assigned based on the experience of a specific person, a problem arises in that a nurse without extensive experience in surgery may be assigned to the surgery in question.

Technical Solution

As an embodiment of the present disclosure, a method of providing information n medical personnel may be provided.

The method according to an embodiment of the present disclosure may include: receiving surgical information including information on a medical treatment department performing a surgery, information on an operating surgeon, surgical category information, and surgical code information; determining a score for each item that constitutes the surgical information on medical personnel on the basis of information on on-duty records of the medical personnel; determining a medical personnel score corresponding to the surgical information on the basis of a weighted value corresponding to the score for the each item; and providing information on the medical personnel that includes the medical personnel score.

The method according to an embodiment of the present disclosure, wherein, the determining of a score for each item may comprise: determining a first score for the each item on the basis of the number of times that each of the medical personnel for the each item participates in the surgeries; determining a second score for the each item on the basis of the time for which each of the medical personnel for the each item participates in the surgeries; and determining the score for the each item on the basis of the first score and the second score.

The method according to an embodiment of the present disclosure, wherein, in the determining of a score for each item may comprise: determining a weighted value of a point in time corresponding to a point in time at which each of the medical personnel participates in the surgeries; and determining the score for the each item by adjusting the first score and the second score on the basis of the weighted value of the point in time.

The method according to an embodiment of the present disclosure, wherein, the determining of a first score for the each item may comprise: determining the first score by normalizing the number of times that each of the medical personnel for the each item participates in the surgeries to fall within the same range, and wherein the determining of a second score for the each item may comprise: determining the second score by normalizing the time for which each of the medical personnel for the each time participates in the surgeries to fall within the same range.

The method according to an embodiment of the present disclosure, wherein, the providing of information on the medical personnel may comprise: providing a list in which the medical personnel is ranked, on the basis of the medical personnel score.

The method according to an embodiment of the present disclosure, wherein, may further comprise: receiving additional information including information on a manager, information on off-duty and on-duty days of the medical personnel, and information on assignment of the medical personnel, wherein the providing of the information on medical personnel may comprise: providing the information on the medical personnel on the basis of the medical personnel score and the additional information.

The method according to an embodiment of the present disclosure may further comprise: receiving information on a location where the surgery is performed, wherein the providing of the information on the medical personnel may comprise: matching the information on the location where the surgery is performed with information on a location corresponding to the medical personnel; and providing the information on medical personnel on the basis of the result of the matching.

The method according to an embodiment of the present disclosure may further comprise: receiving evaluation information of the medical personnel score; and modifying the weighted value on the basis of the evaluation information.

The method according to an embodiment of the present disclosure may further comprise: updating the information on on-duty records of the medical personnel at a predetermined time interval.

The method according to an embodiment of the present disclosure, wherein, the information on on-duty records includes information on the time at which each of the medical personnel who participates in the surgeries starts to work on a per-surgery basis, information on the time at which each of the medical personnel ends working, information on an operating room, the information on the medical treatment department, the information on the operating surgeon, the surgical code information and information on surgery time.

As an embodiment of the present disclosure, an electronic apparatus may be provided.

The apparatus according to an embodiment of the present disclosure may include: a memory configured in such a manner that at least one instruction is stored therein; and a processor configured to execute the instruction stored in the memory, thereby receiving surgical information including information on a medical treatment department performing a surgery, information on an operating surgeon, surgical category information, and surgical code information, determining a score for each item that constitutes the surgical information on medical personnel on the basis of information on on-duty records of the medical personnel, determining a medical personnel score corresponding to the surgical information on the basis of a weighted value corresponding to the score for the each item, and providing information on the medical personnel that includes the medical personnel score.

The apparatus according to an embodiment of the present disclosure, wherein, the processor may determine a first score for the each item on the basis of the number of times that each of the medical personnel for the each item participates in the surgeries, determine a second score for the each item on the basis of the time for which each of the medical personnel for the each item participates in the surgeries, and determine the score for the each item on the basis of the first score and the second score.

The apparatus according to an embodiment of the present disclosure, wherein, the processor may determine a weighted value of a point in time corresponding to a point in time at which each of the medical personnel participates in the surgeries, and determine the score for the each item by adjusting the first score and the second score on the basis of the weighted value of the point in time.

The apparatus according to an embodiment of the present disclosure, wherein, the processor may determine the first score by normalizing the number of times that each of the medical personnel for the each item participates in the surgeries to fall within the same range, and determine the second score by normalizing the time for which each of the medical personnel for the each time participates in the surgeries to fall within the same range.

The apparatus according to an embodiment of the present disclosure, wherein, the processor may provide a list in which the medical personnel is ranked, on the basis of the medical personnel score.

The apparatus according to an embodiment of the present disclosure, wherein, the processor may receive additional information including information on a manager, information on off-duty and on-duty days of the medical personnel, and information on assignment of the medical personnel, and provide the information on the medical personnel on the basis of the medical personnel score and the additional information.

The apparatus according to an embodiment of the present disclosure, wherein, the processor may receive information on a location where the surgery is performed, match the information on the location where the surgery is performed with information on a location corresponding to the medical personnel, and provide the information on medical personnel on the basis of the result of the matching.

The apparatus according to an embodiment of the present disclosure, wherein, the processor may receive evaluation information of the medical personnel score, and modify the weighted value on the basis of the evaluation information.

The apparatus according to an embodiment of the present disclosure, wherein, the processor may update the information on on-duty records of the medical personnel at a predetermined time interval.

BRIEF DESCRIPTION OF THE DRAWINGS

Figure 1A:
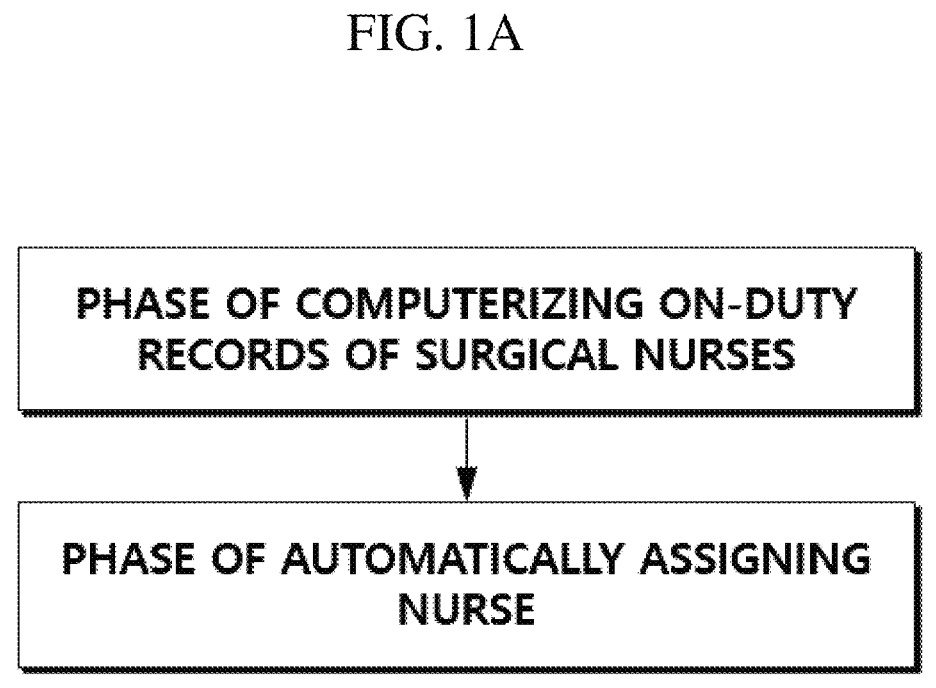

FIG. 1A is a block diagram that is referenced to describe a system for providing information on medical personnel according to an embodiment of the present disclosure.

FIGS. 2A and 2B are tables showing examples of the information on on-duty records of medical personnel in the method of providing information on medical personnel according to an embodiment.

FIGS. 3A and 3B are tables each illustrating a method of determining a medical personnel score according to an embodiment of the present disclosure.

FIG. 4 is a diagram illustrating an example of the interface through the surgical information is input, which is provided by a terminal according to an implementation example.

FIG. 5 is a diagram illustrating an example of a search information input interface according to an implementation example.

FIG. 6 is a diagram illustrating an example of an interface for providing information on medical personnel.

DETAILED DESCRIPTION

Figure 1B:
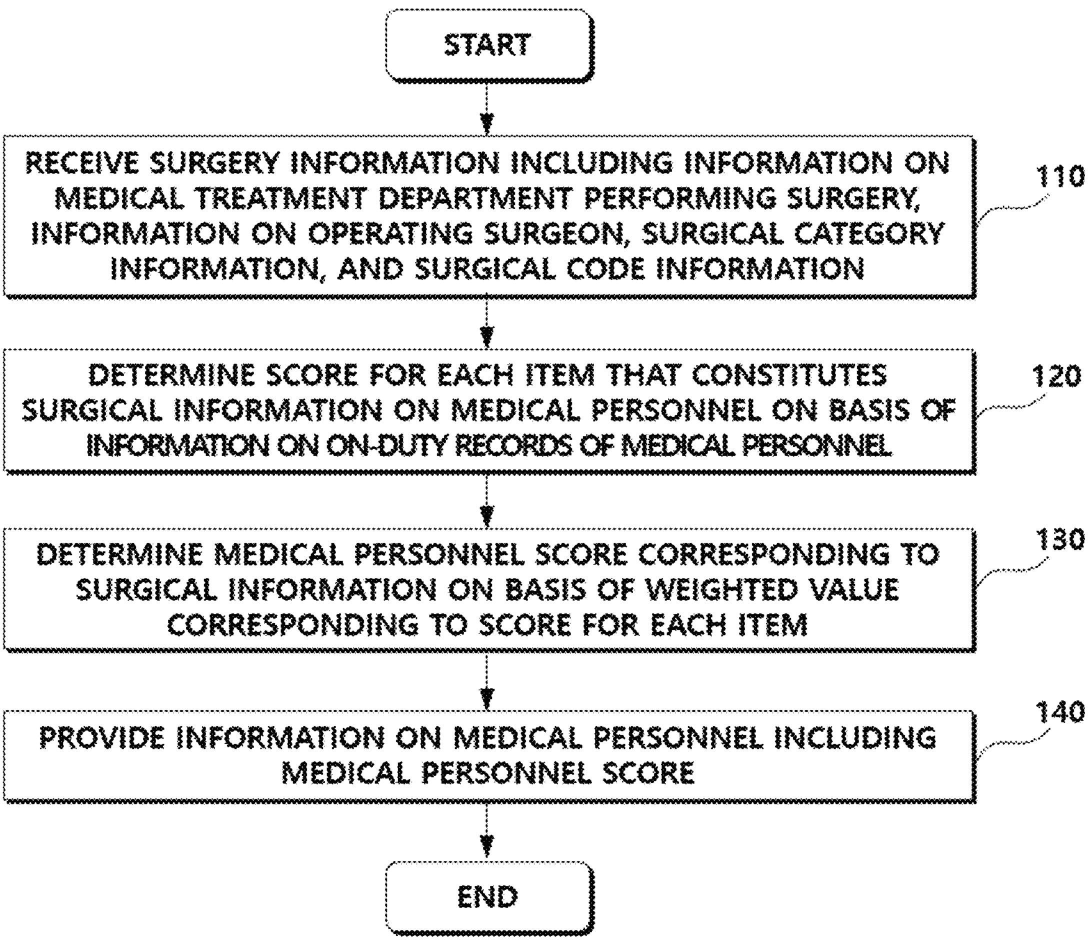
FIG. 1B is a flowchart that is referenced to describe a method of providing information on medical personnel according to an embodiment of the present disclosure.

Hereinafter, embodiments of the present invention will be described with reference to the drawings. In the following description, descriptions of a well-known technical configuration in relation to a lead implantation system for a deep brain stimulator will be omitted. For example, descriptions of the configuration/structure/method of a device or system commonly used in deep brain stimulation, such as the structure of an implantable pulse generator, a connection structure/method of the implantable pulse generator and a lead, and a process for transmitting and receiving electrical signals measured through the lead with an external device, will be omitted. Even if these descriptions are omitted, one of ordinary skill in the art will be able to easily understand the characteristic configuration of the present invention through the following description.

FIG. 1A is a block diagram that is referenced to describe a system for providing information on medical personnel according to an embodiment of the present disclosure.

The medical personnel is hereinafter primarily described as surgical nurses (may be hereinafter referred to as nurses) on duty who participate in medical treatments (for example, surgeries), but this term is not limited to these nurses. For example, the medical personnel may include doctors other than operating surgeons (in a broad sense, such as dentists and oriental medical doctors), as well as physical therapists, occupational therapists, nurse assistants, and others.

With reference to FIG. 1A, when performing a specific surgery in a hospital, the system for providing information on medical personnel according to an embodiment may provide information for assigning the most competent surgical nurse suited for such a surgery.

The system for providing information on medical personnel according to an embodiment may perform a step of computerizing on-duty records of surgical nurses and a step of automatically assigning a surgical nurse. The step of computerizing on-duty records of surgical nurses may refer to computerizing data (for example, raw data) related to on-duty records of surgical nurses. The step of computerizing on-duty records of surgical nurses is in detail described with reference to FIGS. 2A and 2B. The step of automatically assigning a surgical nurse may include a step of setting a logic for assigning the most competent surgical nurse suited for a specific surgery when performing such a surgery.

The system for providing information on medical personnel according to an embodiment may include a server and a terminal as entities. The server and the terminal may be connected to each other through a network, and thus information may be readily transmitted and received between them.

A terminal according to an implementation example may acquire surgical information, information on on-duty records of medical personnel, and search information and may transfer them to the server. The surgical information includes information on a medical treatment department performing a surgery, information on an operating surgeon, surgical category information, and surgical code information.

The terminal according to the implementation example may refer to any electronic apparatus on which an application for providing information on medical personnel (hereinafter referred to as an application), which is associated with the server, can be installed and be run. In this case, the terminal may perform operations associated with an overall service, such as service screen configuration, data input, data transmission and reception, and data storage, under the control of the application. The application may be realized in such a manner as to run in a mobile environment, as well as in a PC environment. The application may be realized in the form of a program that runs independently. Alternatively, the application may be configured in the form of an in-app component within a specific application and thus may be realized in such a manner as to run on the specific application.

The terminal may provide an interface through which surgical information, information on on-duty records, and search information. The terminal may provide an interface through which information on medical personnel corresponding to the surgical information is output. To this end, the terminal may include a display. Examples of the interfaces provided by the terminal are described below with reference to FIGS. 4 to 6.

The server may determine a score for each item that constitutes surgical information of medical personnel, on the basis of the surgical information and the information on on-duty records that are received from the terminal. Furthermore, the server may determine a medical personnel score that corresponds to the surgical information, on the basis of a weighted value corresponding to the score for each item, and may transfer to the terminal the information on the medical personnel that includes the medical personnel score.

A system for providing information on medical personnel according to an embodiment of the present disclosure may be configured to include only a terminal without a server. In this case, the terminal may determine a score for each item that constitutes surgical information of medical personnel, on the basis of the surgical information and the information on on-duty records. Furthermore, the terminal may determine a medical personnel score that corresponds to the surgical information, on the basis of a weighted value corresponding to the score for each item, and may provide the information on the medical personnel that includes the medical personnel score.

FIG. 1B is a flowchart that is referenced to describe a method of providing information on medical personnel according to an embodiment of the present disclosure.

The description with reference to FIG. 1A may similarly apply to FIG. 1B. Identical descriptions may not be repeated. For convenience of description, Steps 110 to 140 are described as being performed in the system for providing information on medical personnel that is described with reference to FIG. 1A. However, Steps 110 to 140 may also be performed through another suitable electronic apparatus or within another suitable system.

Moreover, operations in FIG. 1B may be performed in the order and manner that are illustrated. However, the order of several of the operations may be changed or one or several of the operations may be omitted, without departing from the scope of the technical idea of the method according to an embodiment that is illustrated. Many of the operations illustrated in FIG. 1B may be performed serially or concurrently.

With reference to FIG. 1B, in Step 110, the system for providing information on medical personnel according to an embodiment may receive the surgical information that includes the information on a medical treatment department performing a surgery, the information on an operating surgeon, the surgical category information, and the surgical code information. The information on a medical treatment department refers to information related to a medical treatment department that participates in the surgery in question. A plurality of medical treatment departments may participate in a single surgery. In this case, the information on a medical treatment department may include information on all medical treatment departments that participate in the single surgery. The information on an operating surgeon may include information (for example, the name of the operating surgeon, the medical treatment department to which the operating surgeon belongs, the rank of the operating surgeon, and the like) on the operating surgeon who performs the operation in question. The surgical category information refers to information of a category to which the surgeon belongs, and the category may be present in a stepwise manner. For example, all surgeries are categorized into major, medium, and minor classes. The surgical code information may be unique information that is assigned to each surgery, such as a management code or a claim code that is managed in the hospital in question. A terminal according to an implementation example may provide an interface through which surgical information is input, and a user may input the surgical information through the interface provided by the terminal. The surgical information may include various information associated with the surgery, in addition to the information on a medical treatment department performing a surgery, the information on an operating surgeon, the surgical category information, and the surgical code information that are described above.

In Step 120, the system for providing information on medical personnel according to an embodiment may determine a score for each item that constitutes the surgical information of medical personnel, on the basis of the information on on-duty records of the medical personnel. When performing a specific surgery, the system for providing information on medical personnel according to an embodiment may determine the score for each item that constitutes the surgical information of medical personnel, in order to assign the most competent surgical nurse suited for such a surgery. As described above, the system for providing information on medical personnel may computerize the information on on-duty records of medical personnel before performing the operation in question.

In Step 130, the system for providing information on medical personnel according to an embodiment may determine the medical personnel score corresponding the surgical information, on the basis of the basis of the weighted value corresponding to the score for each item. The medical personnel score may be referred to as a surgical nursing competency score (competency score). The system for providing information on medical personnel may determine medical personnel scores for a medical treatment department, an operating surgeon, a surgical category, and a surgical code that are matched with the surgery in question, on the basis of the number of times that a surgical nurse participates in surgeries and the time for which she/he participates in surgeries.

More specifically, the system for providing information on medical personnel may determine a first score for each item on the basis of the number of times that each of the medical personnel for each item participates in surgeries. Furthermore, the system may determine a second score for each item on the basis of the time for which each of the medical personnel for each item participates in surgeries. Furthermore, the system may determine a score for each item on the basis of the first score and the second score. A specific method of determining the first score and the second score are described below with reference to FIGS. 3A and 3B.

In Step 140, the system for providing information on medical personnel according to an embodiment may provide the information on the medical personnel that includes the medical personnel score. The system for providing information on medical personnel may provide a list in which the medical personnel is ranked, on the basis of the medical personnel score.

The system for providing information on medical personnel may assign the most competent surgical nurse suited for a specific surgery on the basis of the medical personnel score. In a daytime zone during which a manager works, the medical personnel may be assigned considering additional information (for example, a surgical nursing competency update road map for a specific nurse) not reflected in the score. This assignment can be facilitated by utilizing the system capable of preferentially making an inquiry for a nurse having a high medical personnel score for the surgery in question. In an evening or night-time zone during which the manager does not work, nurses in an available medical personnel pool may be automatically assigned in the order of decreasing the medical personnel score for the surgery in question.

FIGS. 2A and 2B are tables showing examples of the information on on-duty records of medical personnel in the method of providing information on medical personnel according to an embodiment.

A medical treatment department other than the medical treatment department that mostly uses a specific operating room may perform a surgery in the specific operating room where a surgical nurse works. In this case, the system for providing information on medical personnel according to an embodiment may y reflect the information on the medical treatment department that actually participates in a surgery, in the surgical nursing competency of the surgical nurse (for example, the specific operating room is initially assigned to a medical treatment department in the morning or in the afternoon, but in a case where this medical treatment department cannot use the specific operating room because a doctor in the department is scheduled to participate in a seminar or for other reasons, another medical treatment department may use the specific operating room). In addition, the system for providing information on medical personnel may reflect surgical code information on a surgery in which a surgical nurse participates, in addition to a specific medical treatment department that participates in a surgery.

With reference to FIG. 2A, the system for providing information on medical personnel may store raw data in such a manner that inquiries are made for a medical treatment department participating in a surgery, an operating surgeon, a surgical code, and surgery time, along with the time at which a surgical nurse starts to work in a specific operating room and the time at which the surgical nurse ends working. The raw data may be stored in a memory in a terminal according to an implementation example and may be stored in a database included in the server.

With reference to FIG. 2B, instead of information on an operating room where the nurse in question works, the system for providing information on medical personnel may map information on a medical treatment department, to which an operating surgeon performs the surgery in question, a surgical code information, and information on the time required for the surgery to each other and may store the result of the mapping. The information on on-duty records of medical personnel that is illustrated in FIGS. 2A and 2B is only an example. The information on on-duty records of medical personnel may be stored in various forms.

FIGS. 3A and 3B are tables each illustrating a method of determining a medical personnel score according to an embodiment of the present disclosure.

With reference to FIG. 3A, the system for providing information on medical personnel may assign scores for a medical treatment department, an operating surgeon, a surgical category, and a surgical code that are matched with the surgery in question, on the basis of the number of times that a surgical nurse participates in surgeries and the time for which she/he participates in surgeries.

For example, when Mr. PYO 00, an operating surgeon in a colorectal anus surgery department, is scheduled to perform a surgery corresponding to the surgical code GSSC00399, the system for providing information on medical personnel may determine a score for each item that constitutes surgical information for the medical personnel, on the basis of the number of times that each of the medical personnel for each item participates in surgeries, and may determine a medical personnel score corresponding to the surgical information on the basis of a weighted value corresponding to the score for each item.

For convenience in comparison, before reflecting a weighted value, values that correspond to scores (for example, x1, x2, x3, x4, y1, y2, y3, and y4), respectively, for all items may be standardly set to have a minimum value of 0 and a maximum value of 100. For example, the system for providing information on medical personnel may standardize a score for each item on the basis of 100*(specific value−minimum value)/(maximum value−minimum value).

In addition, a weighted value of a % may be assigned to a medical treatment department item, a weighted value of b % to an operating surgeon item, a weighted value of c % to a surgical category item, and a weighted value of d % to a surgical code item. In this case, the equation a %+b %+c %+d %=100% should be satisfied.

Moreover, the system for providing information on medical personnel may determine the first score for each item on the basis of the number of times that each of the medical personnel for each item participates in surgeries, and may determine the second score for each item on the basis of the time for which each of the medical personnel for each item participates in surgeries. For example, a weighted value of a % may be assigned to the number of times that each of the medical personnel participates in surgeries, and a weighted value of 3% may be assigned to the time for which each of the medical personnel participates in surgeries. At this case, the equation a %+B %=100% should be satisfied.

The system for providing information on medical personnel may determine a weighted value of a point in time that represents the point in time at which each of the medical personnel participates in a surgery, and may determine a score for each item by adjusting the first score and the second score. For example, the system for providing information on medical personnel may adjust the first score and the second score by assigning a higher weighted value to the later point in time at which each of the medical personnel participates in a surgery.

The user (for example, an operating surgeon) may evaluate the reliability of the medical personnel score of each of the medical personnel who participates in the surgery in question, after finishing the surgery in question. The system for providing information on medical personnel may receive evaluation information and may modify the weighted value on the basis of the evaluation information. For example, in a case where the operating surgeon evaluates the reliability of a score for each of the medical personnel who participates in the surgery in question, as low, the system for providing information on medical personnel may adjust the weighted value in such a manner as to increase the reliability of the medical personnel score.

With reference to FIG. 3B, the system for providing information on medical personnel may prioritize a surgical code, matched with the surgery in question, as the first priority and a medical treatment department, to which a surgeon performing the surgery in question belongs, as the second priority. Under this condition, the system may display the total number of surgeries that the nurse in question, among the medical personnel, and the total amount of time for which she/he participates in surgeries, in descending order. In this case, the total number of surgeries and the total amount of time themselves may refer to the medical personnel score.

FIG. 4 is a diagram illustrating an example of the interface through the surgical information is input, which is provided by a terminal according to an implementation example.

With reference to FIG. 4, the terminal according to the implementation example may provide the interface through which surgical information may be input. By using the terminal, the user may input a medical treatment department, an operating surgeon, a surgical category, a surgical code, location information, and time information. The terminal may additionally provide a search function for the user to input the surgical information. For example, when the user selects a medical treatment department on the interface, information on all medical treatment departments may be provided, and thus, the user may be guided to select one from among them.

Location information according to an implementation example may include information on a location where a surgery is performed. For example, in a case where the surgery in question is performed in an operating room in the main ward, the location information corresponding to the surgery in question may be the operating room in the main ward. Time information according to an implementation example may include information on the time scheduled to perform a surgery and the estimated time taken to perform the surgery.

A category (major, medium, or minor class) for the surgical code in question may be generated, considering the scenario where a personnel pool of surgical nurses that participate in surgeries with specific surgical codes, and this category information may be reflected in the medical personnel score.

Figure 5:
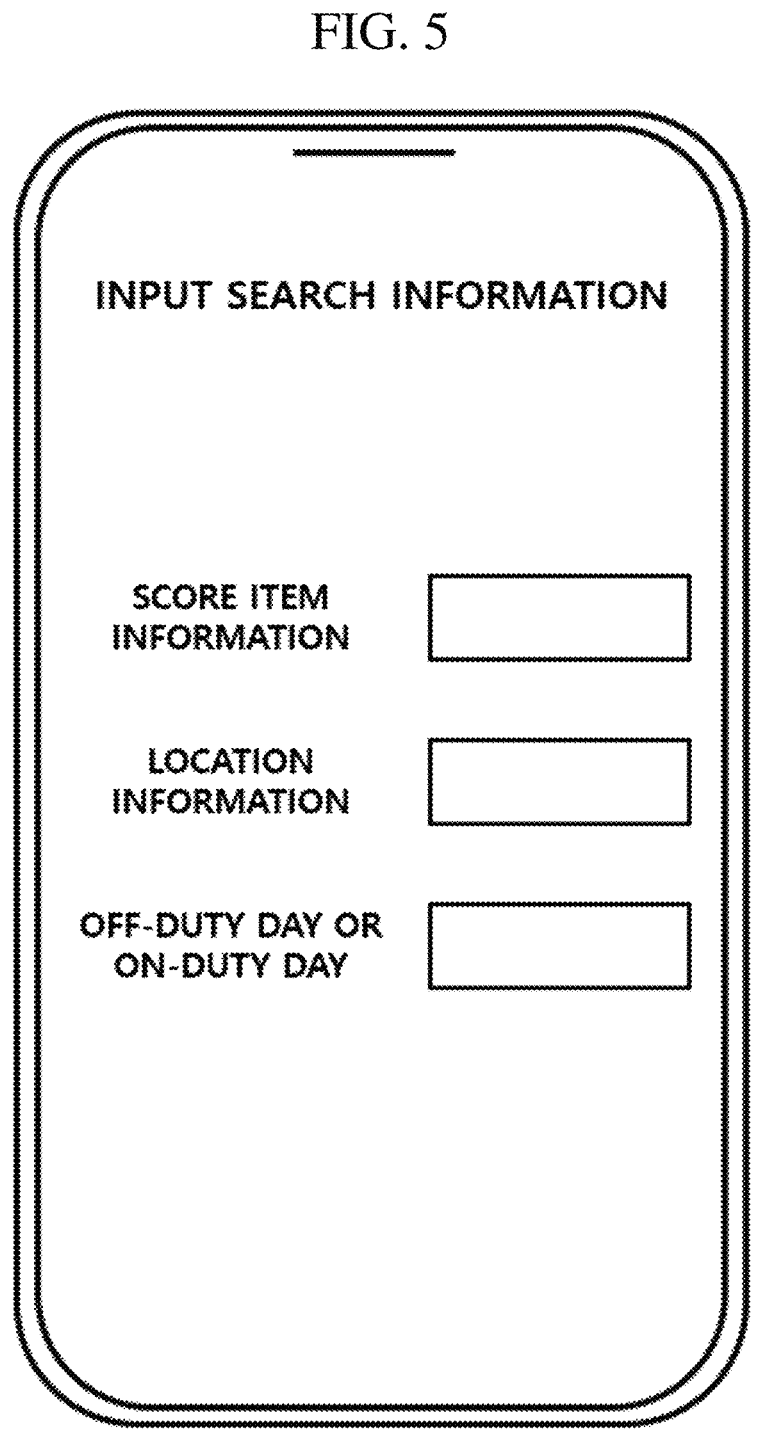

FIG. 5 is a diagram illustrating an example of a search information input interface according to an implementation example.

With reference to FIG. 5, a terminal according to an implementation example may provide the interface through which score item information, location information, and an off-duty day or an on-duty day may be input.

The score item information refers to information related to which score is used to receive information on medical personnel. For example, in a case where the user selects a total score, the terminal may provide the information on medial personal that is arranged on the basis of the total score. In addition, in a case where the user selects a surgical code score, the terminal may provide the information on the medical personnel that is arranged on the basis of the surgical code score.

The location information refers to information on medical personnel who works in a specific location. For example, in a case where the user selects the main ward, the terminal may provide only the information on the medical personnel that works in the main ward. In addition, in a case where the user selects all information on medical personnel, the terminal may provide all information on medical personnel who works in the whole hospital. When an emergency surgery is to be performed in a specific location (for example, in the operating room in the main ward), a personnel pool matched with the specific location may not be present. In this case, accordingly, an inquiry may also be made for a personnel pool in a different location (for example, an operating room in a cancer ward). In a case where the personnel pool matched with the different location is present, this personnel pool may be utilized.

The off-duty day or on-duty day information may indicate whether only information on medical personnel on duty or information on medical personnel both off duty and on duty is provided.

FIG. 6 is a diagram illustrating an example of an interface for providing information on medical personnel.

With reference to FIG. 6, a terminal according to an implementation example may provide the information on the medical personnel that includes a name, a medical personal score (for example, a total score), location information, and off-duty and on-duty information. In the list in question, the medical personnel scores may be arranged in descending order.

The user may select medical personnel most suited for the surgery in question with reference to the interface for providing information on medical personnel or may automatically assign medical personnel having the highest medical personnel score to the surgery in question.

Figure 7:
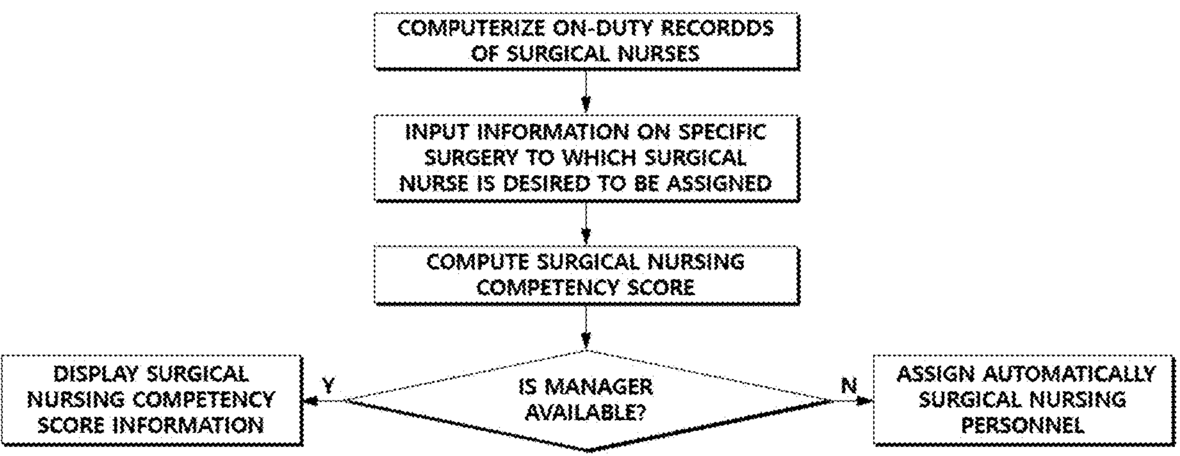
FIG. 7 is a flowchart that is referenced to describe a method of operating the system for providing information on medical personnel according to an embodiment of the present disclosure.

FIG. 7 is a flowchart that is referenced to describe a method of operating the system for providing information on medical personnel according to an embodiment of the present disclosure.

With reference to FIG. 7, the method of operating the system for providing information on medical personnel according to an embodiment includes a step of computerizing on-duty records of surgical nurses, a step of inputting information on a specific surgery to which a surgical nurse is desired to be assigned, and a step of computing surgical nursing competency score. The method may include a step of displaying information on the surgical nursing competency score and a step of automatically assigning surgical nurse personnel, depending on whether or not a manager is absent.

More specifically, in the step of computerizing on-duty records of surgical nurses, information on surgeries in which the surgical nurse participates may be secured on the basis of 'a medical treatment department, an operating surgeon, a surgical code, and surgery time.'

In the step of inputting information on a specific surgery to which a surgical nurse is desired to be assigned, a location where a surgery is to be performed (for example, the main ward, annexed ward, or cancer ward), a medical treatment department performing a surgery, an operating surgeon, and surgical code information may be input.

In the step of computing a surgical nursing competency score, scores for a personnel pool of surgical nurses who are available in the surgery location in question may be computed with reference to 'medical treatment department, an operating surgeon, a surgical category, and a surgical code' and 'the number of times of participation and participation time,' on the basis of the input surgical information.

In the step of displaying the information on the surgical nursing competency score, in a daytime zone during which a manager works, a system for making an inquiry for related information may be realized in such a manner as to more efficiently assign surgical nurse personnel who is to participate in a specific surgery.

The manager may provide information necessary to assign both 'n' surgical nurses with high competency for the surgery in question and 'm' surgical nurses who need to improve their competency of the surgery in question, considering a road map for updating the competency of specific surgical nurses, along with the information in question.

In the step of automatically assigning surgical nurse personnel, the surgical nurses may be assigned in the order of decreasing competency scores, on the basis of information on the competency scores computed for the personnel pool of surgical nurses that are available in the surgery location in question. In a case where the personnel matched with the surgery location in question is not available, a personnel pool in a different location may be further used.

Figure 8:
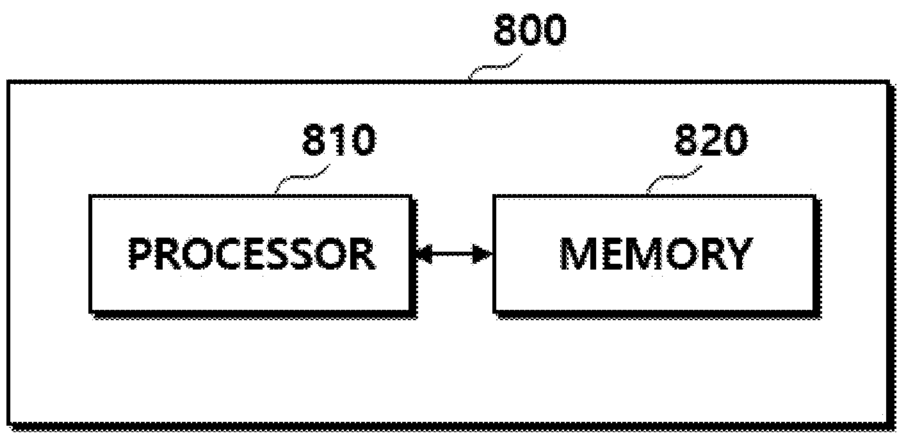
FIG. 8 is a diagram illustrating a configuration of an electronic apparatus according to an embodiment of the present disclosure.

FIG. 8 is a diagram illustrating a configuration of an electronic apparatus 800 according to an embodiment of the present disclosure.

With reference to FIG. 8, the electronic apparatus 800 may include one or more processor 810 and a memory 820.

Instructions readable from a computer may be stored in a memory 820 according to an implementation example. When the instructions stored in the memory 820 are executed by the processor 810, the processor 810 may perform operations defined by the instructions. Example of the memory 820 may include a random access memories (RAMs), dynamic random access memories (DRAMs), static random access memories (SRAMs), and other types of non-volatile memories that are known in the technical field.

One or more processors 810 according to an implementation example may control the overall operation of the electronic apparatus 800. The processor 810 may be a device that is realized in hardware having a circuit employing a physical structure for performing desired operations. The desired operations may involve the execution of codes or instructions included in a program. The devices realized in hardware may include a microprocessor, a central processing unit (CPU), a graphic processing unit (GPU), a processor core, a multi-core processor, a multiprocessor, an application-specific integrated circuit (ASIC), a field programmable gate array (FPGA), a neural processing unit (NPU), and the like.

A processor 810 according to an implementation example may receive surgical information including information medical treatment department performing a surgery, information on an operating surgeon, surgical category information, and surgical code information. Furthermore, the processor 810 may determine a score for each item that constitutes surgical information on medical personnel, on the basis of information on on-duty records of the medical personnel. Furthermore, the processor 810 may determine medical personnel score corresponding to the surgical information, on the basis of a weighted value corresponding to the score for each item, and may provide information on medical personnel, which includes the medical personnel score.

The embodiments described above may be implemented by hardware components, software components, and/or any combination thereof. For example, the devices, the methods, and components described in the embodiments may be implemented by using general-purpose computers or special-purpose computers, such as a processor, a controller, an arithmetic logic unit (ALU), a digital signal processor, a microcomputer, a field programmable gate array (FPGA), a programmable logic unit (PLU), a microprocessor, or any other devices which may execute and respond to instructions. A processing apparatus may execute an operating system (OS) and a software application executed in the OS. Also, the processing apparatus may access, store, operate, process, and generate data in response to the execution of software. For convenience of understanding, it may be described that one processing apparatus is used. However, one of ordinary skill in the art will understand that the processing apparatus may include a plurality of processing elements and/or various types of processing elements. For example, the processing apparatus may include a plurality of processors or a processor and a controller. Also, other processing configurations, such as a parallel processor, are also possible.

The software may include computer programs, code, instructions, or any combination thereof, and may construct the processing apparatus for desired operations or may independently or collectively command the processing apparatus. In order to be interpreted by the processing apparatus or to provide commands or data to the processing apparatus, the software and/or data may be permanently or temporarily embodied in any types of machines, components, physical devices, virtual equipment, computer storage mediums, or transmitted signal waves. The software may be distributed over network coupled computer systems so that it may be stored and executed in a distributed fashion. The software and/or data may be recorded in a computer-readable recording medium.

A method according to an embodiment may be implemented as program instructions that can be executed by various computer devices, and recorded on a computer-readable recording medium. The computer-readable recording medium may include program instructions, data files, data structures or a combination thereof. Program instructions recorded on the medium may be particularly designed and structured for embodiments or available to one of ordinary skill in a field of computer software. Examples of the computer-readable recording medium include magnetic media, such as a hard disc, a floppy disc, and magnetic tape; optical media, such as a compact disc-read only memory (CD-ROM) and a digital versatile disc (DVD); magnetooptical media, such as floptical discs; and hardware devices specially configured to store and execute program instructions, such as ROM, random-access memory (RAM), a flash memory, etc. Program instructions may include, for example, high-level language code that can be executed by a computer using an interpreter, as well as machine language code made by a complier.

In concluding the detailed description, those skilled in the art will appreciate that many variations and modifications may be made to the preferred embodiments without substantially departing from the principles of the present invention. Therefore, the disclosed preferred embodiments of the invention are used in a generic and descriptive sense only and not for purposes of limitation.

What is claimed is:

1. A method of providing information on medical personnel, the method comprising:

receiving surgical information including information on a medical treatment department performing a surgery, information on an operating surgeon, surgical category information, and surgical code information;

determining, by a processor, a score for each item that constitutes the surgical information on medical personnel on the basis of information on on-duty records of the medical personnel, the on-duty records including a history of surgeries in which each of the medical personnel has previously participated;

determining, by the processor, a medical personnel score corresponding to the surgical information on the basis of a weighted value corresponding to the score for each item, wherein the medical personnel score represents a surgical nursing competency of each of the medical personnel derived from the on-duty records;

providing information on each of the medical personnel that includes the medical personnel score;

evaluating, by the operating surgeon after finishing the surgery, a reliability of the medical personnel score of at least one of the medical personnel who participated in the surgery to generate evaluation information input via an interface provided on a terminal;

receiving, by the processor, the evaluation information generated by the operating surgeon after finishing the surgery;

modifying, by the processor, the weighted value on the basis of the evaluation information so as to increase the reliability of the medical personnel score; and automatically assigning, by the processor, an available one of the medical personnel to the surgery by selecting, from a personnel pool of available medical personnel at a location where the surgery is to be performed, the medical personnel having a highest medical personnel score corresponding to the surgical information, and transmitting assignment information of the selected medical personnel to the terminal;

wherein the determining of the score for each item further comprises:

determining a first score for each item on the basis of the number of times that each of the medical personnel for each item participates in the surgeries;

determining a second score for each item on the basis of the time for which each of the medical personnel for each item participates in the surgeries; and determining the score for each item on the basis of the first score and the second score.

2. The method of claim 1, wherein in the determining of the score for each item further comprises:

determining a weighted value of a point in time corresponding to a point in time at which each of the medical personnel participates in the surgeries; and determining the score for the each item by adjusting the first score and the second score on the basis of the weighted value of the point in time, wherein a later point in time at which each of the medical personnel participates in a surgery is assigned a higher weighted value than an earlier point in time.

3. The method of claim 1, wherein the determining of the first score for each item further comprises:

determining the first score by normalizing the number of times that each of the medical personnel for the each item participates in the surgeries to fall within a same range, and wherein the determining of the second score for the each item comprises:

determining the second score by normalizing the time for which each of the medical personnel for the each time participates in the surgeries to fall within the same range.

4. The method of claim 1, wherein the providing of information on the medical personnel comprises:

providing a list in which the medical personnel is ranked, on the basis of the medical personnel score.

5. The method of claim 1, further comprising:

receiving additional information including information on a manager, information on off-duty and on-duty days of the medical personnel, and information on assignment of the medical personnel, wherein the providing of the information on medical personnel comprises:

providing the information on the medical personnel on the basis of the medical personnel score and the additional information.

6. The method of claim 1, further comprising:

receiving information on a location where the surgery is performed, wherein the providing of the information on the medical personnel comprises:

matching the information on the location where the surgery is performed with information on a location corresponding to the medical personnel; and providing the information on medical personnel on the basis of the result of the matching.

7. The method of claim 1, further comprising:

updating the information on on-duty records of the medical personnel at a predetermined time interval.

8. The method of claim 1, wherein the information on on-duty records includes information on the time at which each of the medical personnel who participates in the surgeries starts to work on a per-surgery basis, information on the time at which each of the medical personnel ends working, information on an operating room, the information on the medical treatment department, the information on the operating surgeon, the surgical code information and information on surgery time.

9. A non-transitory computer-readable recording medium having recorded thereon a computer program including instructions executable by the processor to perform the method of claim 1.

10. The method of claim 1, wherein the automatically assigning comprises:

in a daytime zone during which a manager is present, providing the personnel pool ranked by the medical personnel score to the manager via the terminal, thereby enabling the manager to select the medical personnel considering the medical personnel score and a competency update road map for a specific one of the medical personnel; and in an evening or night-time zone during which the manager is absent, automatically assigning the medical personnel from the personnel pool in an order of decreasing medical personnel score.

11. An electronic apparatus comprising:

a memory configured in such a manner that at least one instruction is stored therein; and a processor configured to execute the at least one instruction stored in the memory, thereby:

receiving surgical information including information on a medical treatment department performing a surgery, information on an operating surgeon, surgical category information, and surgical code information;

determining a score for each item that constitutes the surgical information on medical personnel on the basis of information on on-duty records of the medical personnel, the on-duty records including a history of surgeries in which each of the medical personnel has previously participated;

determining a medical personnel score corresponding to the surgical information on the basis of a weighted value corresponding to the score for each item, wherein the medical personnel score represents a surgical nursing competency of each of the medical personnel derived from the on-duty records;

providing information on each of the medical personnel that includes the medical personnel score;

evaluating, by the operating surgeon after finishing the surgery, a reliability of the medical personnel score of at least one of the medical personnel who participated in the surgery to generate evaluation information input via an interface provided on a terminal;

receiving, by the processor, the evaluation information generated by the operating surgeon after finishing the surgery;

modifying the weighted value on the basis of the evaluation information so as to increase the reliability of the medical personnel score; and automatically assigning an available one of the medical professional to the surgery by selecting, from a personnel pool of available medical personnel at a location where the surgery is to be performed, the medical personnel having a highest medical personnel score corresponding to the surgical information, and transmitting assignment information of the selected medical personnel to the terminal;

wherein the determining of the score for each item further comprises:

determining a first score for each item on the basis of the number of times that each of the medical personnel for each item participates in the surgeries;

determining a second score for each item on the basis of the time for which each of the medical personnel for each item participates in the surgeries; and determining the score for each item on the basis of the first score and the second score.

12. The electronic apparatus of claim 11, wherein the processor further:

determines a weighted value of a point in time corresponding to a point in time at which each of the medical personnel participates in the surgeries, and determines the score for the each item by adjusting the first score and the second score on the basis of the weighted value of the point in time, wherein a later point in time at which each of the medical personnel participates in a surgery is assigned a higher weighted value than an earlier point in time.

13. The electronic apparatus of claim 11, wherein the processor further:

determines the first score by normalizing the number of times that each of the medical personnel for the each item participates in the surgeries to fall within a same range, and determines the second score by normalizing the time for which each of the medical personnel for each time participates in the surgeries to fall within the same range.

14. The electronic apparatus of claim 11, wherein the processor further provides a list in which the medical personnel is ranked, on the basis of the medical personnel score.

15. The electronic apparatus of claim 11, wherein the processor further:

receives additional information including information on a manager, information on off-duty and on-duty days of the medical personnel, and information on assignment of the medical personnel, and provides the information on the medical personnel on the basis of the medical personnel score and the additional information.

16. The electronic apparatus of claim 11, wherein the processor further:

receives information on a location where the surgery is performed, matches the information on the location where the surgery is performed with information on a location corresponding to the medical personnel, and provides the information on medical personnel on the basis of the result of the matching.

17. The electronic apparatus of claim 11, wherein the processor further updates the information on on-duty records of the medical personnel at a predetermined time interval.

18. The electronic apparatus of claim 11, wherein the processor is further configured to:

in a daytime zone during which a manager is present, provide the personnel pool ranked by the medical personnel score to the manager via the terminal, thereby enabling the manager to select the medical personnel considering the medical personnel score and a competency update road map for a specific one of the medical personnel; and in an evening or night-time zone during which the manager is absent, automatically assign the medical personnel from the personnel pool in an order of decreasing medical personnel score.

* * * * *